US00PP08633P

United States Patent [19]

Zary

[11] Patent Number: Plant 8,633

[45] Date of Patent: Mar. 8, 1994

[54] HYBRID TEA ROSE PLANT NAMED 'JACSLING'

[75] Inventor: Keith W. Zary, Thousand Oaks, Calif.

[73] Assignee: Bear Creek Gardens, Inc., Medford, Oreg.

[21] Appl. No.: 998,238

[22] Filed: Dec. 15, 1992

[51] Int. Cl.[5] ..... A01H 5/00

[52] U.S. Cl. ..... Plt./20

[58] Field of Search ..... Plt. 20, 21

*Primary Examiner*—Howard J. Locker

*Attorney, Agent, or Firm*—Klarquist, Sparkman, Campbell, Leigh and Whinston

[57] ABSTRACT

A hybrid tea class rose plant having a bright red stable flower color; long, straight stems; vigorous, upright growth; good yield or cut flowers; good vase life; and thick, heavy petals.

1 Drawing Sheet

The present invention relates to a new and distinct variety of rose plant of the Hybrid tea class which was originated by me by crossing the variety KORlingo, U.S. Plant Pat. No. 5,846, with an unnamed seedling.

The primary objective of this breeding was to produce a new rose variety having the excellent petal substance and bright red color of KORlingo and the longer stems of the unnamed seedling. The objective was substantially achieved along with other desirable improvements as evidenced by the following unique combination of characteristics which are outstanding in the new variety and which distinguish it from its parents, as well as from all other varieties of which I am aware:

1. Vigorous upright habit of growth;
2. Long, strong, straight stems;
3. Bright red, stable flower color;
4. Thick, heavy petal substance;
5. Good yield (175 to 200 stems per $m^2$) and good vase life.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—KORlingo, U.S. Pat. No. 5,846.

*Pollen parent.*—An unnamed seedling.

Classification:

*Botanical.*—Rosa hybrida.

*Commercial.*—Hybrid tea.

FLOWER

Observations made from specimens grown in a greenhouse environment in Somis, Calif., from January through June, 1992.

Blooming habit: Recurrent.

Bud:

*Size.*—2" when the petals start to unfurl.

*Form.*—Long, pointed ovoid.

*Color.*—When sepals first divide, bud color is Red Group 44A. When half blown, the upper and lower sides of the petals are Red Group 44A.

*Sepals.*—Color: Green Group 138B. Surface texture: Covered with fine hairs. There are three normally appendaged sepals. There are two unappendaged sepals with hairy edges.

*Receptacle.*—Color: Green Group 137B. Shape: Funnel. Size: Broad, ⅜" wide ×2/8" long. Surface: Smooth.

*Peduncle.*—Length: Medium, 3" to 3½". Surface: Smooth with occasional glands. Color: Medium green. Strength: Stiff, erect.

Bloom:

*Size.*—Large. Average open size is 4½".

*Borne.*—Singly.

*Stems.*—Long, strong, 22–26".

*Form.*—When first open: High centered. Permanence: Outer petals curl back.

*Petalage.*—Number of petals under normal conditions: 25.

*Color.*—The upper and reverse sides of the petals are Red Group 44A. The bases of the petals have a distinct yellow half moon at the point of attachment (⅜"×⅜"). The major color on the upper side is Red Group 44A.

*Variegations.*—None.

*Discoloration.*—The general tonality at the end of the first day: no change. At the end of the third day: No change.

*Fragrance.*—Slight.

Petals:

*Texture.*—Thick, leathery.

*Shape.*—Round to slightly deltoid.

*Form.*—Tips slightly recurved.

*Arrangement.*—Imbricated, with no petaloids in the center.

*Persistence.*—Drop off cleanly.

*Lastingness.*—On the plant: Long, 5 to 6 days. As a cut flower: Long, 8 to 9 days.

Reproductive Parts:

*Anthers.*—Size: Medium. Quantity: Many. Color: Light yellow. Arrangement: Regular around the styles.

*Filaments.*—Color: Reddish.

*Pollen.*—Color: Lemon yellow.

*Styles.*—Color: Reddish.

*Stigmas.*—Color: Greenish white.

Form: Bush.

Growth: Vigorous, upright and branching.

Foliage: Number of leaflets on normal mid-stem leaves: 5.

*Size.*—Large, 6"×4".

*Quantity.*—Abundant.

*Color.*—New foliage: Reddish. Old foliage: Dark green.

Leaflets:

*Shape.*—Pointed oval.

*Texture.*—Upper side: Smooth and semi-glossy.

*Edge.*—Serrated.

*Serration.*—Single and small.

*Petiole Rachis.*—Color: Green.

*Petiole Underside.*—Smooth.

*Stipules.*—Short.

*Disease Resistance.*—Susceptible to mildew under normal growing conditions in a greenhouse environment at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when young.*—Red.

Small Prickles:

*Quantity.*—On main stalks: None. On laterals: None.

I claim:

1. A new and distinct variety of rose plant of the hybrid tea class, substantially as herein shown and described, characterized particularly as to novelty by the unique combination of its bright red stable flower color, its long, straight stems, its vigorous, upright growth, its good yield of cut flowers, its good vase life and its thick, heavy petals.

* * * * *

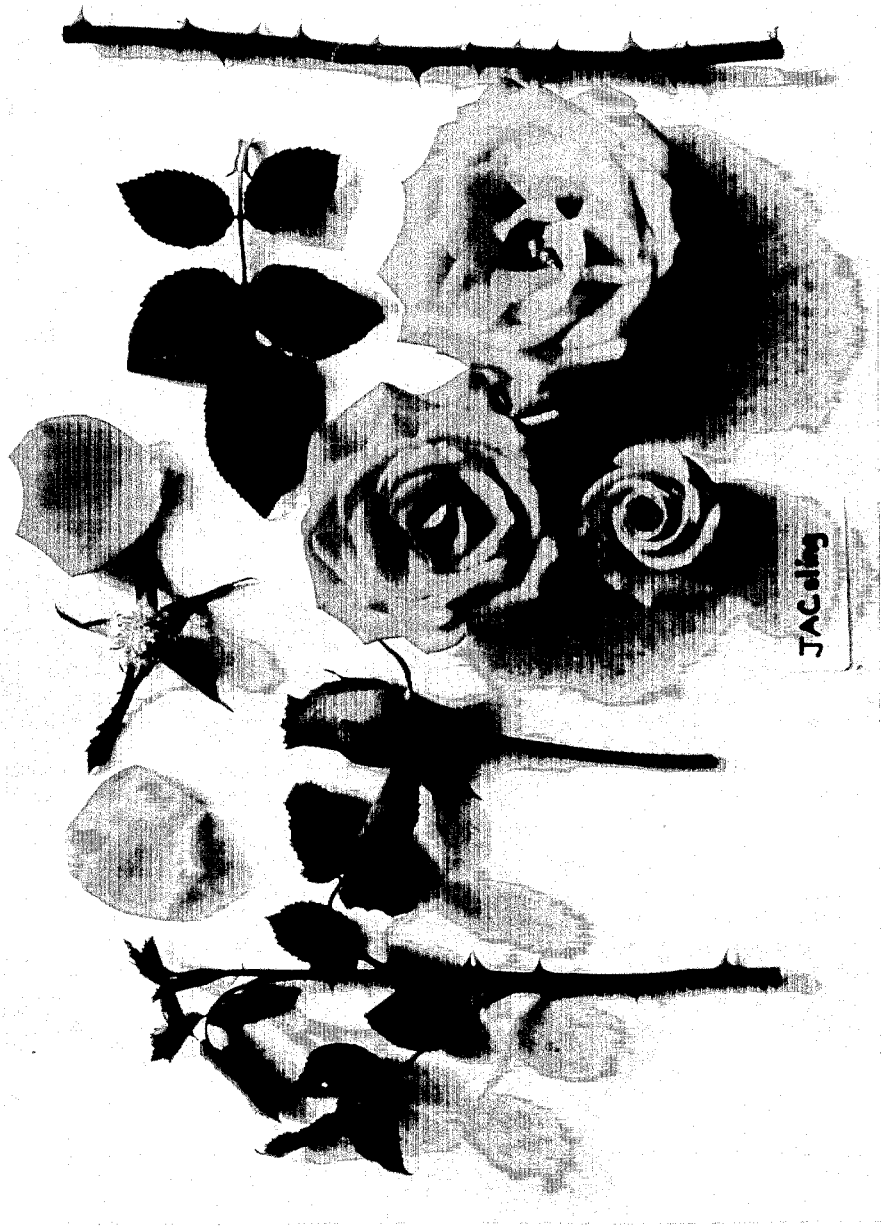
JAColling